United States Patent [19]

Edward

[11] 4,199,976

[45] Apr. 29, 1980

[54] HARDNESS TESTING APPARATUS

[75] Inventor: John C. Edward, Beaumont, Tex.

[73] Assignee: J B Development Corporation, Beaumont, Tex.

[21] Appl. No.: 944,548

[22] Filed: Sep. 21, 1978

[51] Int. Cl.² ............................................. G01N 3/48
[52] U.S. Cl. ..................................................... 73/81
[58] Field of Search ..................... 73/81, 82, 83, 85; 294/65.5; 269/8, 88, 96

[56] References Cited

U.S. PATENT DOCUMENTS

| | | | |
|---|---|---|---|
| 2,544,205 | 3/1951 | Williams | 73/81 |
| 3,389,597 | 6/1968 | Williams | 73/81 |
| 3,795,334 | 3/1974 | Ishida et al. | 294/65.5 X |
| 3,984,092 | 10/1976 | Fitzpatrick | 269/96 X |

OTHER PUBLICATIONS

Edwards, A., Magnetic Tools, from The Engineer (British), Aug. 11, 1961, p. 226.

*Primary Examiner*—Jerry W. Myracle
*Attorney, Agent, or Firm*—Bill B. Berryhill

[57] ABSTRACT

Apparatus for testing hardness properties of materials may comprise: a clamping assembly including a housing in which is carried a magnet for magnetically attaching the apparatus to the material being tested and a head assembly having a penetrator member mounted for engagement with said material being tested and for limited axial movement from a first position to a second position; an actuator connected to the penetrator member for applying predetermined loads thereto; and an indicator responsive to axial movement of the penetrator member to measure the hardness of the material.

9 Claims, 4 Drawing Figures

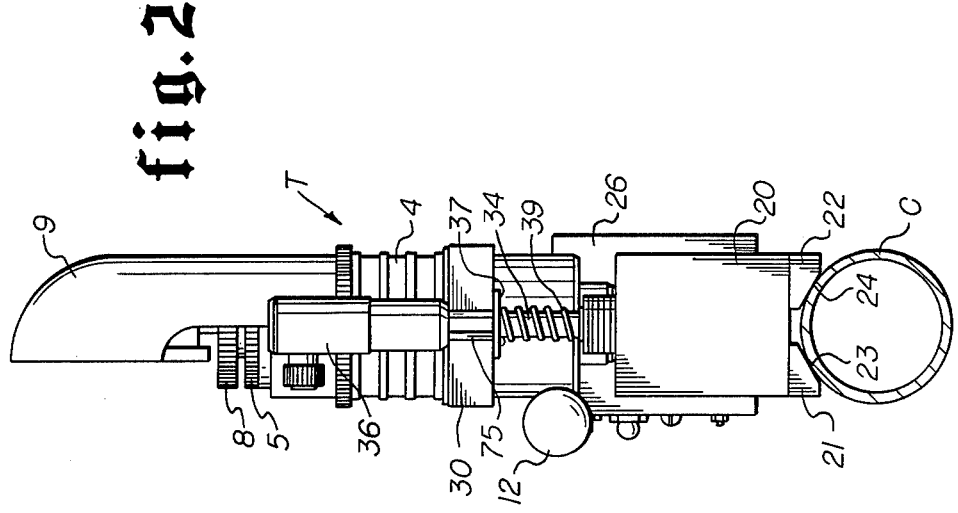
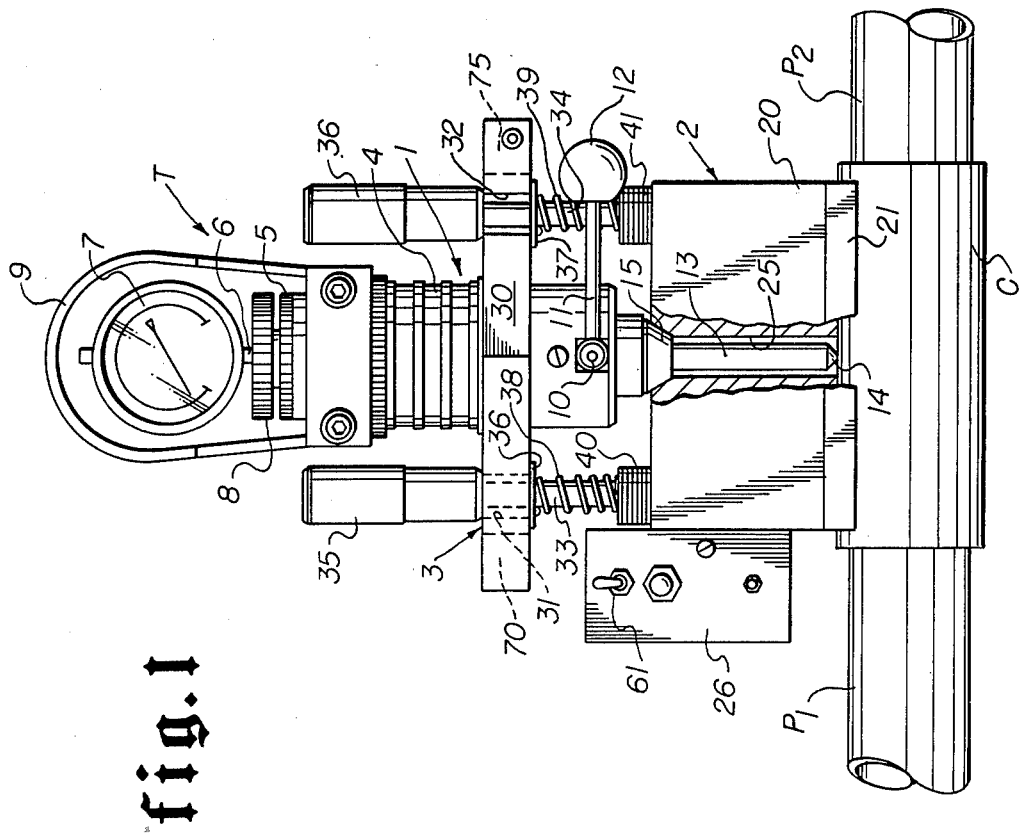

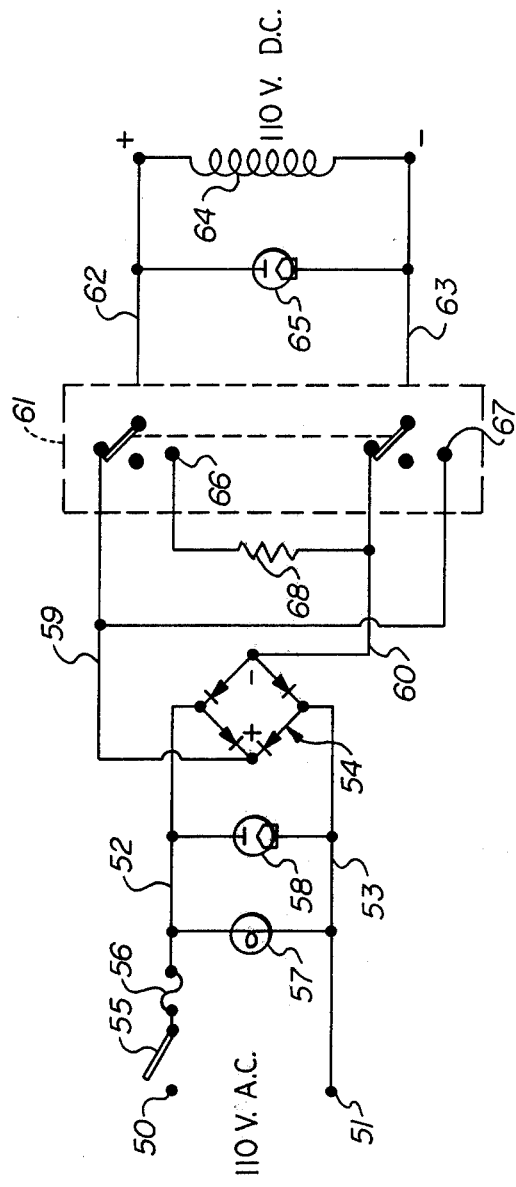
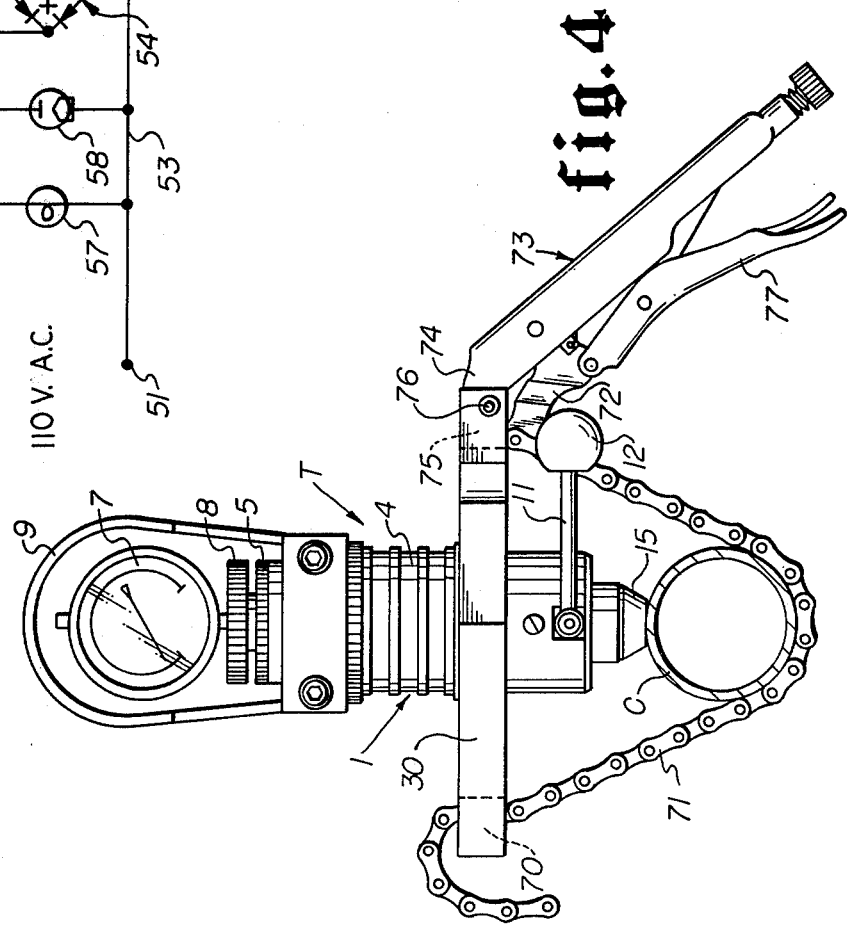

HARDNESS TESTING APPARATUS

BACKGROUND OF THE INVENTION

1. Field of the Invention

The present invention pertains to apparatus for testing properties of materials. Specifically, it pertains to apparatus for testing the hardness properties of materials.

2. Brief Description of the Prior Art

It is frequently necessary to determine certain physical properties and characteristics of materials. This is particularly true in the production of metal goods where a particular range of properties such as hardness may be specified or required in the production thereof. Hardness, as generally applied to physical properties of materials such as metals, can be measured by determining resistance to penetration. Several scales or standards of reference for hardness of materials have been developed over the years. Two of the most common scales are the Rockwell and Brinell hardness scales.

Various testing methods have been developed to indicate or measure the hardness properties of materials. These hardness testing methods usually measure indentation or penetration of a penetrating device to which predetermined loads are applied. Commonly, the penetrating device, upon clamping of the material to be tested within the tester, is placed against the material with a minor or preliminary load. Then a full or major load is applied to the penetrator. The difference of penetration of the material between the minor and major load is measured, on a suitable indicator. This measurement then gives an indication of the hardness of the material.

With many testers of the prior art, it is necessary to bring the material being tested to the tester for clamping therein prior to the test. This is difficult with particular goods, such as pipe and rods. Furthermore, the clamping of certain goods, such as pipe collars, within testers may result in inaccurate readings due to the deformation of the tested goods, not from penetration but from distortion by the particular clamping mechanism or operation of elements of the testing apparatus.

Because of the problems associated with bringing certain goods, such as pipe, to a tester, mobile testing apparatus have been developed. Mobile testers are normally designed for clamping to the material to be tested without the necessity for a permanent or stationary work table. However, due to the varied and changing testing requirements, mobile testers do no exist which are totally acceptable for many situations, particularly testing the hardness of pipe collars.

SUMMARY OF THE INVENTION

In the present invention, a mobile testing instrument is provided which is suitable for testing of many types of goods, but is particularly suitable for the testing of pipe and pipe collars. The apparatus comprises a housing in which is carried an electromagnet for magneticly attaching the testing apparatus to the material to be tested. Like other hardness testers, it is provided with a shaft member having a penetrator on one end thereof engageable with the material being tested and which is mounted for limited axial movement from a first position to a second position in response to predetermined loads applied thereto. An actuator device is connected to the shaft member for axial movement thereof and an indicator device is provided which is responsive to axial movement of the shaft member to measure the hardness of the material.

The particular arrangement of the electromagnet of the tester of the present invention and the circuitry provided therefor is unique. Furthermore, the tester is designed so that the magnetic components may be removed for replacement with a chain clamping device for use in other applications. The testing apparatus is not only one which is unique in its mobility but one which is extremely versatile in its application. Furthermore, it is relatively inexpensive to manufacture. Many other objects and advantages of the invention will be apparent from reading the following specification in conjunction with the accompanying drawings.

BRIEF DESCRIPTION OF THE DRAWINGS

FIG. 1 is a side elevation view, partially broken away, illustrating a hardness tester according to a preferred embodiment of the invention, and being used to test the hardness of a pipe coupling;

FIG. 2 is an end elevation view of the hardness tester of FIG. 1 being used to test a pipe collar;

FIG. 3 is a schematic representation of the electrical circuitry for use in the hardness tester of FIGS. 1 and 2, according to a preferred embodiment of the invention; and FIG. 4 is a side elevation view of the hardness tester of FIGS. 1 and 2 in which the magnetic mounting assembly thereof has been removed and replaced by a chain clamping device, according to an alternate embodiment of the invention.

DESCRIPTION OF THE PREFERRED EMBODIMENTS

Referring first to FIGS. 1 and 2, the hardness tester T of the present invention is shown being used to measure the hardness of a pipe collar C connecting pipe joints $P_1$ and $P_2$. The tester T comprises a head assembly 1 attached to a magnetic clamping assembly 2 by mounting assembly 3.

The head assembly 1 comprises a cylindrical housing 4 in which is contained a conventional load cell (not shown). The load cell is retained in the cylindrical housing 4 at its upper end by a threaded cap 5 having a central opening therethrough (not shown) in which is disposed the stem 6 of a dial gauge 7. The stem 6 of the dial gauge 7 may be rigidly clamped in this disposition in any suitable manner. As illustrated, it is held by a wedge or collet device (not shown) maintained by a lock nut 8. A protective cage or cover 9 may be provided for protecting the dial gauge 7.

At the base of cylindrical housing 4 is an operating cam 10 to which is attached an operating handle and knob, 11 and 12, respectively, the purpose of which will be more fully understood hereafter. The design of the operating cam 10 is known and the details thereof will not be explicitly described. It is sufficient to note that the cam 10 extends through the lower end of the cylindrical housing 4 in the manner of a shaft for contact with the lower end of the load cell contained in housing 4 and with the upper end of a shaft member 13 having a penetrator 14 on the lower end thereof. A threaded penetrator cap 15 may be provided for replacing the shaft and penetrator, 13 and 14, as will be more fully described hereafter.

The magnetic clamping assembly 2 comprises a box-like housing 20 in which is disposed the coils (not shown) of an electromagnet. Along the base of the box-like structure 20 is a pair of removable elongated pole shoes 21 and 22 which are so placed relative to the electromagnetic coil that one of the shoes will be electrically charged of one polarity while the other is of the opposite polarity. As shown each of the shoes 21 and 22 may be provided with inclined surfaces 23 and 24 which allow the shoes 21 and 22 to rest on a rounded surface such as coupling C in a solidly supported position. It will be noted that a vertical opening 25 is provided through the electromagnet housing 20 to centrally receive the penetrator shaft 13 so that the penetrator 14 may rest against coupling C. Fastened to one end of the housing 20 is a circuit box 26 within which certain electrical components, to be more fully described hereafter with reference to FIG. 3, are enclosed.

The head assembly 1 is attached to the magnetic clamping assembly 2 by the mounting assembly 3 which includes a frame or yoke 30 which is attached to the cylindrical housing 4 of the tester assembly 1. The frame 30 is provided with holes 31 and 32 for receiving studs 33 and 34 threaded at the lower ends thereof for threaded engagement with tapped holes provided in the upper portion of the housing 20. The upper end of studs 33 and 34 are provided with increased diameter portions 35 and 36 for hand manipulation. The increased diameter portions 35 and 36 also provide downwardly facing shoulders for resting against frame 30. The washers 36 and 37 rest against the lower surface or frame 30. The washers 36 and 37 are biased against the frame 30 by helical springs 38 and 39. Other washers 40 and 41 may be provided at the base of the springs 38 and 39. It will be noted that the holes 31 and 32 in the frame 30 open toward opposite sides of the frame 30 so that by a slight rotation of the tester head 1 and frame 30, in a counter-clockwise direction, the holes will disengage the studs 33 and 34 for removal of the head assembly 1 from the test of the testing apparatus. So removed, the head assembly 1 and frame 30 may be adapted for chain mounting which will be more fully described hereafter with reference to FIG. 4.

Referring now to FIG. 3, the electrical circuitry of the circuit box 26 will be more fully described. The circuitry may include a pair of input terminals 50 and 51 for connection to a one-hundred-ten volt AC power source. These terminals may be connected through electrical conduits 52 and 53 to a conventional rectifier circuit 54. A power switch 55 and fuse 56 may be provided in one of the conduits. Connected across the conduits may be a pilot light 57 and diode 58 for suppressing transient surges which may arise from the power source. The rectifier 54 converts the AC power to a DC signal through electrical conduits 59 and 60 which are connected to a switch 61 which is preferably a three-position double-pole, double-throw switch, one position which is a momentary position.

The switch 61 as shown in FIG. 3 is in an on position and as such supplies, through conduits 62 and 63, a DC current to coil 64 which represents the electromagnetic coil of the magnetic clamping assembly 2 illustrated in FIGS. 1 and 2. A diode 65 may be connected in parallel with the coil 64 to suppress or filter any current spikes or surges which may be present. The switch 61 is movable to a momentary third position engaging terminals 66 and 67, by which the polarity of coil 64 is temporarily reversed. A resistor 68 may be provided for reducing the power or force of the electromagnetic field created by the coil 64 in the momentary third position. The purpose of the momentary third position will be more fully understood hereafter.

In operation, the testing apparatus T may be placed on the collar C as shown in FIGS. 1 and 2 so that the pole shoes 21 and 22 rest thereon. The electric circuit box 26 may be connected to an AC power source and the switch 61 placed in the "on" position of FIG. 3. Thus, an electromagnetic force is created at the pole shoes 23 and 24 attracting the entire tester apparatus T to the coupling C and holding it firmly in place. The studs 33 and 34 are adjusted by turning the large diameter portions 35 and 36 thereof by hand until the penetrator 14 rests against the collar C as shown in FIG. 1 when the operating handle 11 is in the safety position shown in FIG. 1. Then the operating handle 11 is moved ninety degrees counterclockwise to the minor load position and gauge 7 zeroed. Then, the handle 11 is moved to the major load position (one-hundred-eighty degrees from the position shown in FIG. 1) in which a predetermined load is transferred to the penetrator 14 through shaft 13. The amount of penetration is indicated on the gauge 7 and from the gauge reading, the hardness of the coupling C can be determined.

After the necessary readings are taken, the switch 61 is moved to the "off" position removing current from the coil 64 of the electromagnet housed within the housing 20. However, since there may be some residual magnetism in the pipe, making it difficult to remove the tester apparatus T therefrom, the switch 61 may be moved to the momentary third position in which the field of coil 64 is reversed, changing the polarity of pole shoes 21 and 22. The reverse field then has a tendency to separate the magnetic assembly 2 from the collar C, making it easy to remove.

As earlier noted, the head assembly 1 and frame 30 may be removed from the rest of the tester assembly as has been shown in FIG. 4. The frame 30 can be provided with a slot 70 opening at one end thereof for receiving a chain 71 in a manner conventionally known with chain tongs. The opposite end of the chain 71 may be attached to the lower jaw 72 of a gripping tool 73 which may be conveniently adapted from tools known as "vise grips". The upper jaw or nose 74 of the tool 73 may be adapted for placement in a slot 75 at the opposite end of the frame 30 and may be attached thereto by a pin 76. When used in this manner, the shaft and penetrator assembly 13 and 14 would be removed for replacement by a conventional penetrator (not shown) held in place by the penetrator cap 15.

Adapted as shown in FIG. 4, the tester apparatus T would be placed so as to rest on the upper portion of the coupling C, but with the chain 71 hanging loosely from jaw 72 and with the tool 73 in the open position. Then the free end of chain 71 would be placed in the slot 70 in a position more or less shown in FIG. 4. Then the handle 77 of the tool 73 would be gripped and moved to the closed position, tightening the chain 71 and firmly securing the tester assembly T to the coupling C. Operation from this point on by movement of the handle 11 to the minor and major load positions would be the same as in the previously described embodiment.

As can be well understood, the testing apparatus of the present invention is extremely mobile. It is well adapted for field use, particularly with pipe and other cylindrical materials. The electromagnetic embodiment can be quickly attached and detached from the material being tested. Furthermore, the apparatus is extremely flexible being easily converted to the chain attachment embodiment of FIG. 4.

While two embodiments of the invention have been described herein, many variations of the invention can be made without departing from the spirit of the invention. Accordingly, the scope of the invention is intended to be limited only by the claims which follow.

I claim:

1. Apparatus for testing hardness properties of materials comprising:

a mounting assembly;

a head assembly attached to said mounting assembly having a shaft member with a penetrator on one end thereof for engagement with said material to be tested and mounted for limited axial movement from a first position to a second position in response to predetermined loads applied thereto;

actuator means connected to said shaft member for applying said predetermined loads thereto;

indicator means carried by said head assembly and responsive to said axial movement of said shaft means to measure the hardness of said material; and an electromagnetic clamping assembly to which said mounting assembly is attached and by which said apparatus may be magnetically affixed to said material to be tested, holding said head assembly in a fixed relationship therewith, said electromagnetic assembly comprising an electromagnet disposed in a housing having a first elongated pole along a first side of the base of said housing and a second elongated pole along a second side of the base of said housing so that when said apparatus is attached to tubular material for testing thereof, said poles are in contact with said tubular member through the length of said housing.

2. Testing apparatus as set forth in claim 1 in which a pair of removable shoe members are attached to the base of said housing for contact with said material to be tested, one of said shoe members corresponding with said first pole of said electromagnet and the other of said shoe members corresponding with said second pole of said electromagnet.

3. Testing apparatus as set forth in claim 2 in which said shoe members are provided with inclined surface areas mutually converging toward the center of said housing.

4. Testing apparatus as set forth in claim 1 including an alternating current power source connected to said electromagnet by circuit means including rectifier means for converting alternating current to pulsating direct current.

5. Testing apparatus as set forth in claim 4 in which said circuit means includes switch means between said rectifier means and said electromagnet having an "on" position, in which flow of current is permitted between said rectifier means and said electromagnet and an "off" position, in which flow of current between said rectifier means and said electromagnet is interrupted.

6. Testing apparatus as set forth in claim 4 in which said circuit means includes switch means having a first position, in which flow of current is permitted between said rectifier means and said electromagnet producing one polarity at said first pole and the opposite polarity at said second pole, a second position in which flow of current between said rectifier means and said electromagnet is interrupted; and a third position in which flow of current is permitted between said rectifier means said electromagnet reversing the polarity at said first and second poles.

7. Testing apparatus as set forth in claim 6 in which said circuit means includes resistor means connected between said rectifier means and said electromagnet, when said switch means is in said third position so that the electromagnetic field produced at the poles of said electromagnet is of substantially less strength than the electromagnetic field produced when said switch means is in said first position.

8. Apparatus for testing hardness properties of materials comprising:

a mounting assembly;

a head assembly attached to said mounting assembly having a shaft member with a penetrator on one end thereof for engagement with said material to be tested and mounted for limited axial movement from a first position to a second position in response to predetermined loads applied thereto;

actuator means connected to said shaft member for applying said predetermined loads thereto;

indicator means carried by said head assembly and responsive to said axial movement of said shaft means to measure the hardness of said material; and an electromagnetic clamping assembly to which said mounting assembly is attached and by which said apparatus may be magnetically affixed to said material to be tested, holding said head assembly in a fixed relationship therewith, said mounting assembly including a frame having holes at each end thereof for receiving studs attached to said electromagnetic assembly, one of said holes having an opening toward one side of said frame and the other hole having an opening toward the opposite side of said frame, so that by slight rotation of said frame about the axis of said head assembly, said studs will disengage said holes for removal of said electromagnetic clamping assembly from said apparatus.

9. Testing apparatus as set forth in claim 8 in which the upper end of said studs are provided with increased diameter portions, the diameter of which is greater than the diameter of said holes, spring members being disposed about said studs between said electromagnetic assembly and said frame, biasing said frame against said increased diameter portions of said studs.

* * * * *